United States Patent [19]

Bauer

[11] Patent Number: 4,907,598
[45] Date of Patent: Mar. 13, 1990

[54] GUILLOTINE BIOPSY NEEDLE PROVIDED WITH FLEXIBLE STYLUS AND CANNULA

[76] Inventor: Alberto Bauer, Via Del fosso 1, Pieve Di Cento, Italy

[21] Appl. No.: 183,613

[22] Filed: Apr. 19, 1988

[30] Foreign Application Priority Data

May 5, 1987 [IT] Italy .................. 21519/ 87[U]

[51] Int. Cl.⁴ .............................................. A61B 10/00
[52] U.S. Cl. ................................................... 128/753
[58] Field of Search ............... 128/753, 754, 305, 751; 604/19, 21, 22

[56] References Cited

U.S. PATENT DOCUMENTS

| 4,651,753 | 3/1987 | Lifton | 128/753 |
| 4,702,260 | 10/1987 | Wang | 128/751 |

FOREIGN PATENT DOCUMENTS

| 6513901 | 5/1966 | Netherlands | 128/751 |
| 8201988 | 6/1982 | World Int. Prop. O. | 128/753 |

Primary Examiner—John D. Yasko
Attorney, Agent, or Firm—Ladas & Parry

[57] ABSTRACT

A biopsy guillotine needle, wherein said needle comprises a guillotine portion therewithin a drawing member is able of longitudinally sliding, said drawing member being rigid with the free end of a flexible cable, controlled for sliding within a flexible sheath by control means acting on the opposite end of said flexible cable.

2 Claims, 2 Drawing Sheets

GUILLOTINE BIOPSY NEEDLE PROVIDED WITH FLEXIBLE STYLUS AND CANNULA

BACKGROUND

The present invention relates to a guillotine biopsy needle, the combination and shape of the parts of which provide it with particularly useful characteristics.

Biopsy needles are already known in which the histologic drawing member consists of a pair of tweezers, the closure of which is remotely controlled, the tweezers being mounted at one end of a flexible cable held within a flexible sheath. This assembly is arranged as to afford the possibility of carrying out the histologic drawing even from organs which can only be accessed through a tortuous path including loops and bends.

The aforementioned known needles, on the other hand, are able of performing the drawing operation exclusively on the surface of the organ to be assayed.

Biopsy rigid needles for endotissue drawing operations are moreover known adapted to operate in combination with rigid endoscopes.

However there are not available biopsy flexible needles adapted to cooperate with flexible endoscopes for histologically drawing endotissues.

Accordingly, the main object of the present invention is to provide such a flexible needle for histologically drawing endotissues.

This and other objects of the invention will become more apparent to those skilled in the art from the following disclosure.

More specifically the guillotine biopsy needle according to the invention is essentially characterized in that it comprises a guillotine portion, a drawing member longitudinally slidable with said guillotine portion, said drawing member being rigid with the free end of a flexible cable which is driven for sliding within a flexible sheath by control means acting on the opposite end of said flexible cable.

BRIEF DESCRIPTION OF THE DRAWINGS

The invention is illustrated, by way of an example, in the figures of the accompanying drawings, where.

DETAILED DESCRIPTION

Figure 1:
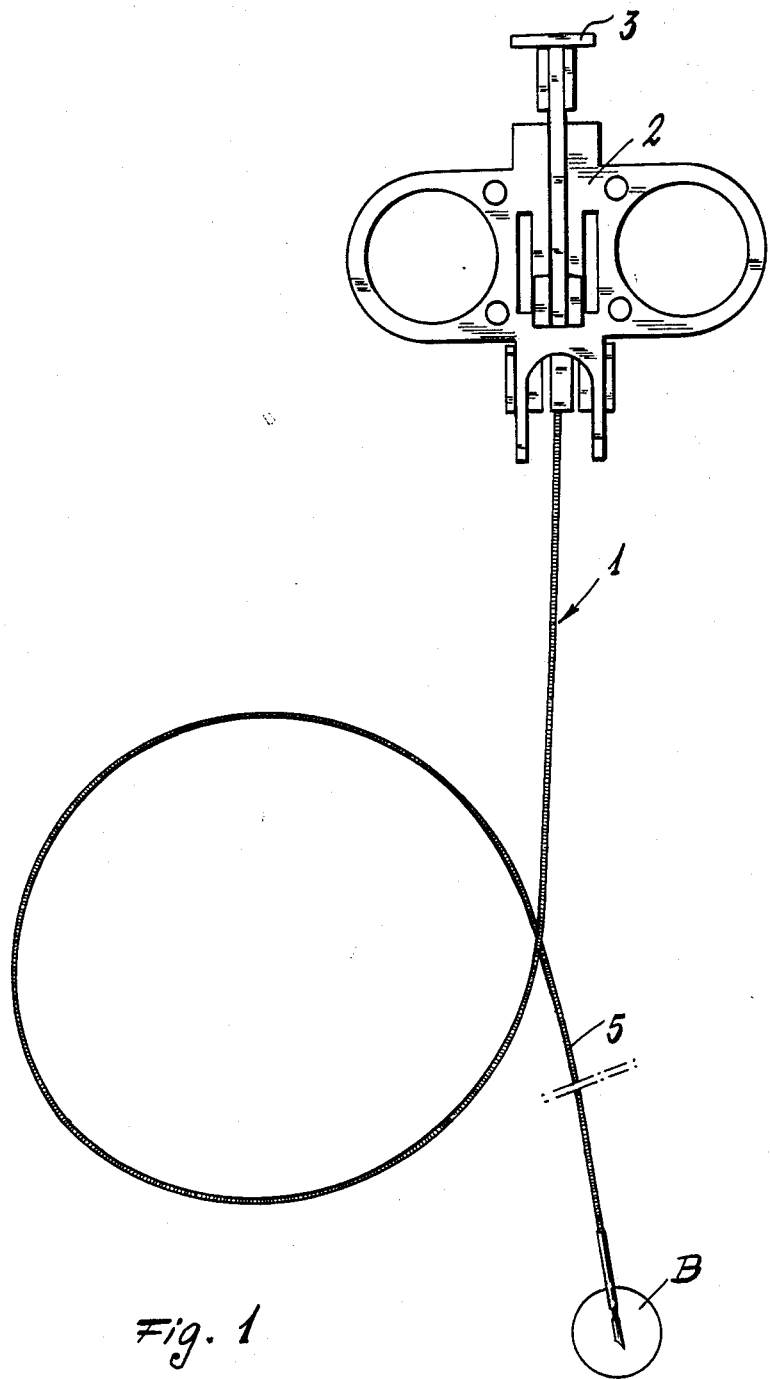
FIG. 1 is an overall view of a biopsy needle according to the invention.
Figure 2:
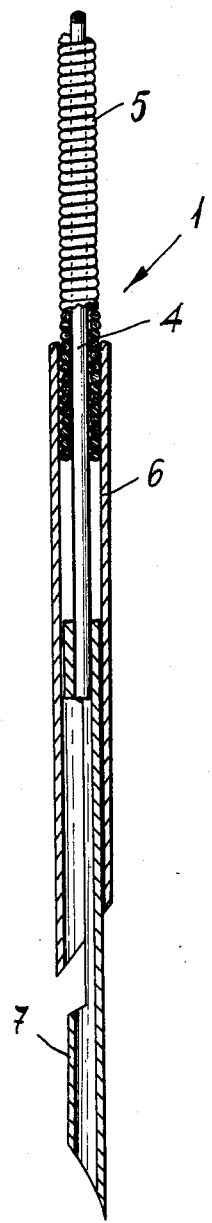
FIG. 2 is an enlarged cross-sectional view of the guillotine drawing member indicated at B in FIG. 1.

With reference to the figures, the biopsy needle, indicated generally at 1 comprises a driving or controlling handle portion 2 including a push button 3 for controlling a flexible cable 4 (FIG. 2) which can slide inside a flexible sheath 5.

The free end of the sheath 5 engages a perforated sleeve 6 therewithin is able of longitudinally sliding the guillotine drawing member 7 which is rigid with the free end of the flexible cable 4.

We claim:

1. A biopsy guillotine needle, characterized in that said needle comprises a guillotine portion therewithin a drawing member (7) is able of longitudinally sliding, said drawing member having a cutting edge at its distal end for entering tissue to be sampled and being rigid with the free end of a flexible cable (4) controlled for sliding within a flexible sheath (5) by control means (2) acting on the opposite end of said flexible cable.

2. A flexible needle for histologically drawing endotissue samples through a flexible endoscope, said needle including an elongated flexible cable, a flexible sheath having a cavity therein in which the flexible cable slides, a drawing member having a cutting edge at its distal end for entering the endotissues to be sampled and having a tissue receiving portion remote from said cutting edge and a sleeve having a cutting edge at its distal end which cooperates with the tissue receiving portion of said drawing member for cutting the endotissue to be sampled, said sleeve being fixed at the end of said flexible sheath.

* * * * *